(12) United States Patent
Brueckner et al.

(10) Patent No.: US 10,864,519 B2
(45) Date of Patent: Dec. 15, 2020

(54) METHOD AND CARTRIDGE FOR DISPENSING PARTICLES AND A REAGENT FLUID IN AN AUTOMATIC ANALYZER

(71) Applicant: Roche Diagnostics Operations, Inc., Indianapolis, IN (US)

(72) Inventors: Thorsten Brueckner, Schriesheim (DE); Nadine Losleben, Munich (DE); Norbert Oranth, Voerstetten (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 290 days.

(21) Appl. No.: 15/819,165

(22) Filed: Nov. 21, 2017

(65) Prior Publication Data

US 2018/0071740 A1 Mar. 15, 2018

Related U.S. Application Data

(63) Continuation of application No. PCT/EP2016/062178, filed on May 30, 2016.

(30) Foreign Application Priority Data

May 29, 2015 (EP) .................................. 15169912

(51) Int. Cl.
*B01L 3/00* (2006.01)
*G01N 35/10* (2006.01)
(Continued)

(52) U.S. Cl.
CPC .............. *B01L 3/523* (2013.01); *B01F 3/12* (2013.01); *B01F 15/0462* (2013.01);
(Continued)

(58) Field of Classification Search
CPC .................................. B01L 3/00; G01N 35/10
(Continued)

(56) References Cited

U.S. PATENT DOCUMENTS 2,905,361 A * 9/1959 Noall .................. B01F 15/0462
222/1
3,489,521 A * 1/1970 Buckle .................... G01N 35/02
422/65
(Continued)

FOREIGN PATENT DOCUMENTS

EP 2662671 * 11/2013
JP H09-61216 A 3/1997
(Continued)

OTHER PUBLICATIONS

International Search Report dated Aug. 4, 2016, in Application No. PCT/EP2016/062178, 4 pp.

*Primary Examiner* — Arlen Soderquist
(74) *Attorney, Agent, or Firm* — Roche Diagnostics Operations, Inc.

(57) ABSTRACT

A method of dispensing a particle mixture and a reagent fluid cartridge are presented. The cartridge comprises a first reservoir partially filled with reagent fluid, a second reservoir partially filled with particles, a pumping chamber, a first pumping chamber conduit connecting the first reservoir and the pumping chamber, a second pumping chamber conduit connecting the second reservoir and the pumping chamber, an outlet for dispensing reagent fluid and particles from the cartridge, an outlet conduit connecting the outlet to the pumping chamber, and a valve sealing the outlet conduit. The method comprises closing the valve, applying a force to the plunger to transport a first defined volume of reagent fluid and second defined volume of particles into the pumping chamber to form a mixture of reagent fluid and particles, opening the valve, and forcing the mixture from the pumping chamber using the plunger to dispense the mixture from the outlet.

21 Claims, 8 Drawing Sheets

(51) Int. Cl.
    *B01F 15/04*    (2006.01)
    *B01F 3/12*    (2006.01)
    *G01N 33/53*    (2006.01)
    *G01N 35/00*    (2006.01)

(52) U.S. Cl.
    CPC .......... *B01L 3/502* (2013.01); *G01N 33/5304* (2013.01); *G01N 35/1002* (2013.01); *B01L 2200/04* (2013.01); *B01L 2200/0647* (2013.01); *B01L 2200/16* (2013.01); *B01L 2300/0867* (2013.01); *B01L 2400/0478* (2013.01); *B01L 2400/0622* (2013.01); *B01L 2400/0644* (2013.01); *G01N 2035/00574* (2013.01)

(58) Field of Classification Search
    USPC .......... 436/43–54, 166, 179–180; 422/63–67
    See application file for complete search history.

(56) References Cited

U.S. PATENT DOCUMENTS

| | | | | |
|---|---|---|---|---|
| 3,525,591 | A * | 8/1970 | Jungner | G01N 35/026 422/66 |
| 3,574,064 | A * | 4/1971 | Binnings | G01N 35/00029 435/286.4 |
| 3,622,279 | A * | 11/1971 | Moran | G01N 35/021 422/65 |
| 3,708,264 | A * | 1/1973 | Jottier | G01N 35/02 436/48 |
| 3,770,382 | A * | 11/1973 | Carter | G01N 35/026 422/65 |
| 3,786,963 | A * | 1/1974 | Metzler, III | B05B 11/3081 222/136 |
| 3,832,135 | A * | 8/1974 | Drozdowski | G01N 35/028 436/47 |
| 3,883,305 | A * | 5/1975 | Hoskins | G01N 35/02 422/65 |
| 4,070,156 | A * | 1/1978 | Moran | G01N 35/1002 422/509 |
| 4,351,799 | A * | 9/1982 | Gross | G01N 35/1016 422/522 |
| 4,483,927 | A * | 11/1984 | Takekawa | G01N 35/026 422/547 |
| 4,503,012 | A * | 3/1985 | Starr | B01L 3/0203 222/386.5 |
| 4,793,524 | A * | 12/1988 | Starr | B01J 4/02 222/309 |
| 4,836,038 | A * | 6/1989 | Baldwyn | G01N 30/24 73/864.21 |
| 4,844,868 | A * | 7/1989 | Rokugawa | G01N 35/021 422/64 |
| 5,232,664 | A * | 8/1993 | Krawzak | G01N 35/1002 422/523 |
| 5,232,666 | A * | 8/1993 | Longman | G01N 35/1016 141/130 |
| 5,288,374 | A * | 2/1994 | Watanabe | G01N 33/492 204/409 |
| 5,358,691 | A * | 10/1994 | Clark | B01L 3/08 422/63 |
| 5,397,539 | A * | 3/1995 | Hayashi | G01N 35/00594 422/552 |
| 5,645,114 | A * | 7/1997 | Bogen | B01L 3/0293 141/130 |
| 5,679,575 | A * | 10/1997 | Kubota | G01N 35/10 422/63 |
| 6,063,339 | A * | 5/2000 | Tisone | B01J 19/0046 422/509 |
| 6,311,740 | B1 * | 11/2001 | Sperry | B29B 7/7678 141/100 |
| 6,405,609 | B1 * | 6/2002 | Richards | G01N 1/312 422/552 |
| 6,471,917 | B1 * | 10/2002 | Velkovska | B01J 19/0046 422/534 |
| 6,589,791 | B1 * | 7/2003 | LaBudde | B01L 3/0265 137/7 |
| 6,780,648 | B1 * | 8/2004 | Sun | G01N 21/6452 422/503 |
| 9,341,641 | B2 * | 5/2016 | Boehm | G01F 11/021 |
| 9,958,468 | B2 * | 5/2018 | Yamashita | G01N 35/0092 |
| 10,330,693 | B2 * | 6/2019 | Boehm | G01N 35/1016 |
| 2001/0025859 | A1 * | 10/2001 | Dumont | B05B 11/3081 222/136 |
| 2002/0064483 | A1 | 5/2002 | Sando et al. | |
| 2002/0064880 | A1 * | 5/2002 | Merten | B67C 3/206 436/43 |
| 2002/0164821 | A1 * | 11/2002 | Brink | G01F 11/021 436/180 |
| 2002/0192113 | A1 * | 12/2002 | Uffenheimer | G01N 15/1404 422/67 |
| 2003/0040104 | A1 * | 2/2003 | Barbera-Guillem | C12M 23/24 435/286.2 |
| 2003/0040105 | A1 | 2/2003 | Sklar et al. | |
| 2003/0164386 | A1 * | 9/2003 | Connelly | G01F 11/16 222/361 |
| 2005/0003458 | A1 * | 1/2005 | Moore | B01J 19/0046 435/7.2 |
| 2005/0277912 | A1 * | 12/2005 | John | A61M 5/1408 604/890.1 |
| 2008/0080302 | A1 | 4/2008 | Takahashi | |
| 2008/0159915 | A1 | 7/2008 | Yu et al. | |
| 2009/0110606 | A1 * | 4/2009 | Fukushima | G01N 35/1016 422/400 |
| 2009/0176314 | A1 * | 7/2009 | Steinboeck | B01L 3/502 436/174 |
| 2009/0253181 | A1 * | 10/2009 | Vangbo | G01N 27/44791 435/91.1 |
| 2010/0015009 | A1 * | 1/2010 | Wallace | B01L 3/0268 422/400 |
| 2010/0064825 | A1 * | 3/2010 | Bell | G01N 1/14 73/863.83 |
| 2011/0236990 | A1 * | 9/2011 | Mizutani | G01N 35/00603 436/180 |
| 2011/0243793 | A1 * | 10/2011 | Kalin | H02P 8/14 422/67 |
| 2012/0241045 | A1 * | 9/2012 | Aouad | B01F 1/0038 141/83 |
| 2012/0279990 | A1 * | 11/2012 | Werner | B05B 11/3083 222/132 |
| 2013/0105042 | A1 * | 5/2013 | Brown | B01F 13/1055 141/9 |
| 2013/0273591 | A1 | 10/2013 | Attinger et al. | |
| 2015/0122837 | A1 * | 5/2015 | Werner | B05B 11/3083 222/145.6 |
| 2015/0140669 | A1 | 5/2015 | Boehm et al. | |
| 2015/0231658 | A1 * | 8/2015 | Werner | B05B 11/3069 222/145.6 |
| 2016/0139164 | A1 * | 5/2016 | Brueckner | G01N 35/1002 436/501 |
| 2016/0216289 | A1 * | 7/2016 | Augstein | G01N 35/1002 |
| 2018/0220647 | A1 * | 8/2018 | Bingham | A01N 31/02 |

FOREIGN PATENT DOCUMENTS

| | | |
|---|---|---|
| WO | 2010/115192 A2 | 10/2010 |
| WO | 2015/018626 A1 | 2/2015 |

* cited by examiner

US 10,864,519 B2

METHOD AND CARTRIDGE FOR DISPENSING PARTICLES AND A REAGENT FLUID IN AN AUTOMATIC ANALYZER

CROSS-REFERENCE TO RELATED APPLICATIONS

This application is a continuation of PCT/EP2016/062178, filed May 30, 2016, which is based on and claims priority to EP 15169912.1, filed May 29, 2015, which is hereby incorporated by reference.

BACKGROUND

The present disclosure relates to the dispensing of a defined volume of a reagent fluid and particles.

In medical laboratories, in vitro diagnostic tests are commonly performed on biological samples. Such tests may be performed manually using pipettes or may be performed using an automatic analyzer. Automatic analyzers may automatically add reagents to the biological sample in order to determine the amount of a substance of interest in a biological sample. Automatic analyzers are known in the prior art such as, for example, an automatic analyzer

SUMMARY

According to the present disclosure, a cartridge for an automatic analyzer is presented. The cartridge can comprise a first reservoir at least partially filled with a reagent fluid, a second reservoir at least partially filled with particles, and a pumping chamber. The pumping chamber can be formed from a cavity. The cartridge can further comprise a plunger mounted within the pumping chamber. The plunger can be configured for changing the volume of the pumping chamber. The cartridge can also comprise at least one first pumping chamber conduit connecting the first reservoir and the pumping chamber, at least one second pumping chamber conduit connecting the second reservoir and the pumping chamber, an outlet for dispensing the reagent fluid and the particles from the cartridge, an outlet conduit connecting the outlet to the pumping chamber, and a valve for sealing the outlet conduit.

In accordance with one embodiment of the present disclosure, a method of performing a measurement on a sample containing an analyte using the above cartridge is presented. The method can comprises closing the valve, applying a force to the plunger to transport a first defined volume of reagent fluid and a second defined volume of particles into the pumping chamber to form a mixture of reagent fluid and particles, opening the valve, forcing the mixture in the pumping chamber using the plunger to dispense the mixture from the outlet into a fluid receptacle for mixing with the sample containing an analyte, and performing the measurement on the sample containing an analyte using an analytical unit.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
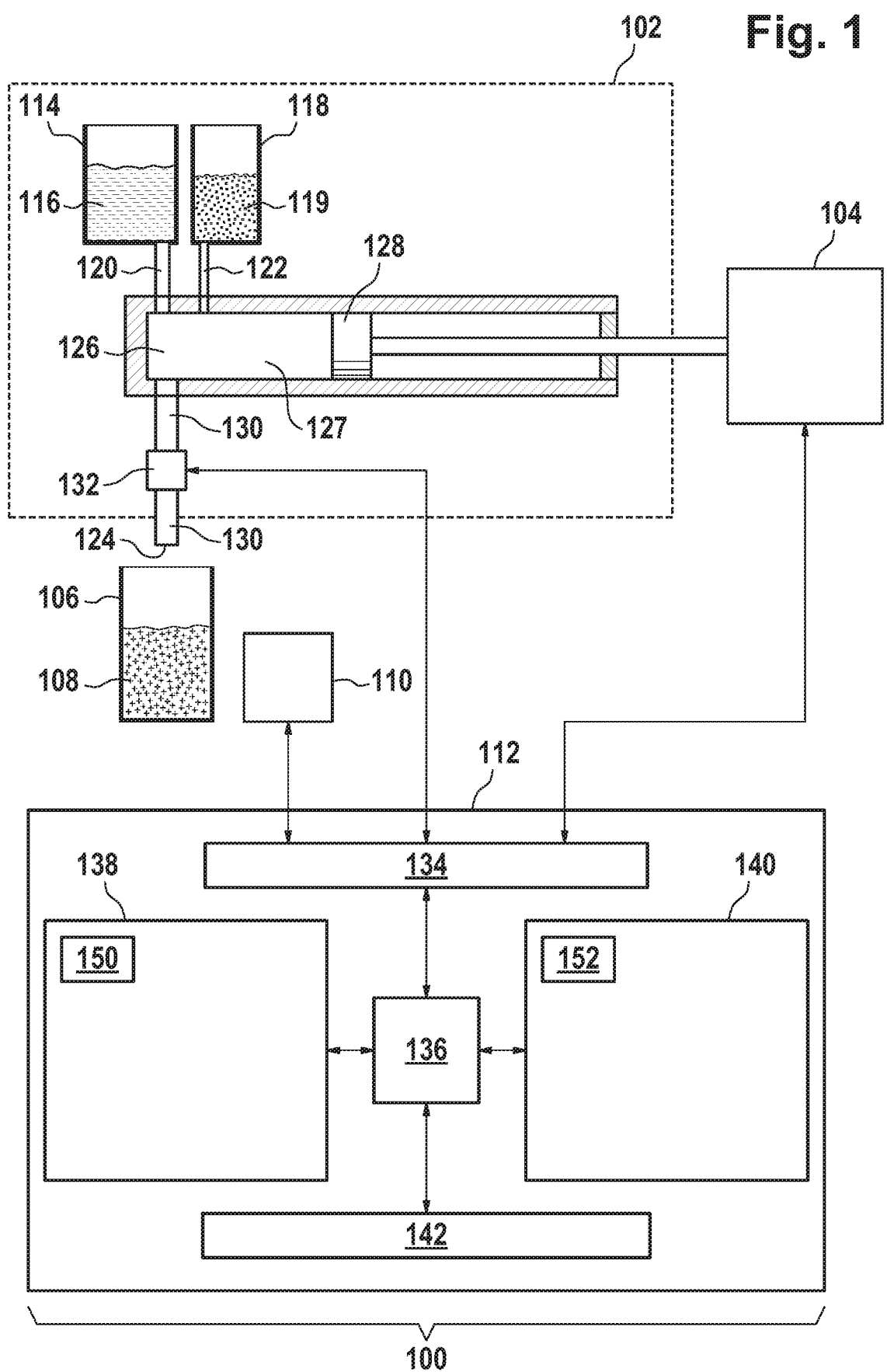
FIG. 1 illustrates an example of an automatic analyzer according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A 'cartridge' as use herein can encompass a case, or container, either containing, or for containing, a fluid which is designed to be inserted into a machine for dispensing the fluid.

A 'controller' as used herein can encompass a device, machine, or apparatus for controlling the operation and/or function of one or more other devices. Examples of a controller may include, but are not limited to: a computer, a processor, an imbedded system or controller, a programmable logic controller, and a microcontroller. A 'computing device' or 'computer' as used herein can encompass any device comprising a processor. A 'processor' as used herein can encompass an electronic component which is able to execute a program or machine executable instruction.

A 'biological sample' as used herein can encompass a sample which can comprise material generated by a biological system. A biological system may include parts, or products, of a living organism or chemicals or materials derived or replicated from an organism. For instance DNA or RNA may be copied by a PCR process although the material is not directly generated by an organism it was derived originally from a biological system or organism.

The term 'analyzer' can refer to a device operable to execute one or multiple analyses on biological samples such as blood, urine, saliva, or other sample types. An analyzer can be operable to determine via various chemical, biological, physical, optical or other technical procedures a parameter of the sample or a component thereof, the parameter in the following being referred to as 'measurement value'. An analyzer can be operable to measure the parameter of the sample or of at least one assay and provide the obtained measurement value. The list of possible analysis results provided by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types.

As will be appreciated by one skilled in the art, aspects of the present disclosure may be embodied as an apparatus, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein can encompass any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium can also refer to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' can be an example of a computer-readable storage medium. Computer memory can be any memory which can be directly accessible to a processor. 'Computer storage' or 'storage' can be a further example of a computer-readable storage medium. Computer storage can be any non-volatile computer-readable storage medium. In some embodiments, computer storage may also be computer memory or vice versa.

A 'processor' as used herein can encompass an electronic component which can be able to execute a program or machine executable instruction or computer executable code. References to the computing device comprising "a processor" can be interpreted as possibly containing more than one processor or processing core. The processor may for instance be a multi-core processor. A processor may also refer to a collection of processors within a single computer system or distributed amongst multiple computer systems. The term computing device can also be interpreted to possibly refer to a collection or network of computing devices each comprising a processor or processors. The computer executable code may be executed by multiple processors that may be within the same computing device or which may even be distributed across multiple computing devices.

Computer executable code or machine executable instructions may comprise machine executable instructions or a program which can cause a processor to perform an aspect of the present disclosure. Computer executable code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which can generate the machine executable instructions on the fly.

The machine executable instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described with reference to flowchart illustrations and/or block diagrams of methods, apparatus (systems) and computer program products according to embodiments of the disclosure. It can be understood that each block or a portion of the blocks of the flowchart, illustrations, and/or block diagrams, can be implemented by computer program instructions in form of computer executable code when applicable.

It can further be understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, can create methods for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which can implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which can execute on the computer or other programmable apparatus provide processes for implementing the functions/acts specified in the flowchart and/or block diagram block or blocks.

A 'hardware interface' as used herein can encompass an interface which can enable the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A method of performing a measurement on a sample containing an analyte using the cartridge is presented. The cartridge can comprise a first reservoir at least partially filled with a reagent fluid. The cartridge can further comprise a second reservoir at least partially filled with particles. In some examples, the second reservoir may be filled entirely with particles and in other examples the second reservoir may contain particles that can be suspended in a fluid of some sort. For example, the fluid may be a different fluid or may also be the reagent fluid. For example, the fluid may be also a gel, for example a thixotropic gel. The cartridge further can comprise a pumping chamber.

The cartridge can further comprise at least one first pumping chamber conduit connecting the first reservoir and the pumping chamber. The cartridge can further comprise at least one second pumping chamber conduit connecting the second reservoir and the pumping chamber. These conduits can connect the first reservoir and the second reservoir to the pumping chamber. The cartridge can further comprise an outlet for dispensing the reagent fluid and the particles from the cartridge. The cartridge can further comprise an outlet conduit connecting the outlet to the pumping chamber. The cartridge can further comprise a valve for sealing the outlet conduit. The valve may be placed in a position, or state, where the outlet conduit can be sealed and the contents of the pumping chamber may not be able to exit through the outlet. The valve may also be put into an open state, or position, so that the contents of the pumping chamber can be able to exit through the outlet.

The method can comprise the step of closing the valve. After the valve has been closed then the outlet conduit can be sealed and the outlet can be isolated from the pumping chamber. The method can further comprise applying a force to transport a first defined volume of reagent fluid and a second defined volume of particles into the pumping chamber to form a mixture of reagent fluid and particles. The method can further comprise opening the valve. The method can further comprise forcing the mixture in the pumping chamber to dispense the mixture from the outlet into a fluid receptacle for mixing with the sample containing an analyte. The method can further comprise the step of performing a measurement on the sample containing the analyte using an analytical unit.

This embodiment may have the benefit that the ratio of the reagent fluid to the particles can be accurately controlled. This embodiment may have the advantage that since the reagent fluid and particles are stored separately, it can be less susceptible to the settling of particles within a reagent fluid. For example, if a pump only had one reservoir which contained both the reagent fluid and the particles, it may be necessary to provide for some sort of mixing or stirring of the particle and reagent fluid mixture. In the current embodiment, the two quantities, the reagent fluid and the particles, can be kept separate and, in the process of pulling them or transporting them to the pumping chamber, the proper amount of each can be extracted from the first and second reservoirs.

In some embodiments, the reagent fluid may be a pure buffer solution. For example, the buffer solution may be water, saline or other buffer solution.

In some examples, the applying of a force to transport the first defined volume and the second defined volume into the pumping chamber may be performed by a sucking or negative pressure. For example, the pumping chamber may be a piston or some other chamber which can be able to increase its volume to apply a sucking force. In other examples, a positive pressure may be applied to the first reservoir and/or the second reservoir. This may be used to transport the defined volumes of the reagent fluid and the particles into the pumping chamber.

In another embodiment the applying of force can be the application of a negative pressure to the pumping chamber. In another embodiment, the step of applying a force can be applying a positive pressure to the first reservoir and/or the second reservoir.

In some examples, the valve can only be configured for closing the outlet conduit. For example, the fluid conductivity of the outlet conduit may be much larger than the at least one first pumping chamber conduit and/or the at least one second pumping chamber conduit. This may enable the use of a single valve for the dispensing of the particles. In this example, when the valve is closed, then the pumping chamber can be used to draw the reagent fluid from the first reservoir and particles from the second reservoir.

When the valve is opened, the mixture in the pumping chamber can be forced through the outlet conduit and because the fluid conductivity of the outlet conduit can be so much larger than the fluid conductivity of the at least one first pumping chamber conduit and/or the at least one second pumping chamber conduit, a negligible amount of the reagent fluid and particle mixture can be forced back through the first or second pumping chamber conduits.

In other examples, the valve may also be operable to not only seal the pumping chamber conduit but also to seal or select the at least one first pumping chamber conduit and/or the at least one second pumping chamber conduit.

In another embodiment, the pumping chamber can be formed at least partially by a cavity. The cartridge can further comprise a plunger mounted movably within the cavity. The plunger can be configured for changing the volume of the pumping chamber. The step of applying the force to transport defined volumes both of reagent fluid and particles into the pumping chamber to form a mixture of reagent fluid and particles within the pumping chamber can comprise expanding the volume of the pumping chamber with the plunger. The step of forcing the mixture in the pumping chamber to dispense the mixture can comprise reducing the volume of the pumping chamber with the plunger.

In another embodiment, the valve can be a throttle valve configured for controlling the first defined volume relative to the second defined volume. For example, the valve may have a component which can control the size of the cross-section of the first pumping chamber conduit relative to the one second pumping chamber conduit. This may be used to control the ratio or mixture of the reagent fluid with respect to the particles.

In another embodiment, the particles can be magnetic particles, in one example, can be magnetic microparticles.

In another embodiment, each magnetic particle can be bound to a complex with a marker, either directly or via other binding partners, the marker being capable of effecting electrochemiluminescence. An electrochemically active substance can contribute to an electrochemiluminescence reaction with the marker resulting in the luminescence.
The method comprises carrying out a reaction sequence comprising at least one analyte-specific biochemical binding reaction to form a complex comprising the analyte-specific marker compound and the analyte as a result of the presence of the analyte in the sample. The complex comprising the marker can be further bound to a magnetic particle. The method further can comprise carrying out a detection cycle on the measurement cell having a working electrode for determining the presence of the analyte. The detection cycle can comprise a capturing step during which the complex can be contacted with a working electrode in such a manner that the particle can be attracted by the magnetic field of a magnetic component positioned on the side of the working electrode facing away from the sample, this being deposited on the surface of the working electrode facing the sample and finally applying a potential to the working electrode that triggered the electrochemiluminescence reaction of the marker with the electrochemically active substance causing the luminescence of the marker to thereby determine the presence of the analyte in the sample.

The feature of applying a force to the plunger to transport a first defined volume of reagent fluid and a second defined volume of particles into the pumping chamber to form a mixture of reagent fluid and particles may be worded in an alternative manner. For example, this may be re-worded as applying a force to the plunger to increase the volume of the pumping chamber. This may cause the transport a first defined volume of reagent fluid and a second defined volume of particles into the pumping chamber to form a mixture of reagent fluid and particles.

The feature of forcing the mixture in the pumping chamber using the plunger to dispense the mixture from the outlet into a fluid receptacle for mixing with the sample containing an analyte may be worded in an alternative manner. For example, this may be re-worded as applying a force to the plunger to decrease the volume of the pumping chamber to dispense the mixture from the outlet into a fluid receptacle for mixing with the sample containing an analyte.

In another embodiment, the method can further comprise applying a force to transport a first defined volume of reagent fluid and a second defined volume of particles into the pumping chamber to form a mixture of reagent fluid and particles can comprise expanding the volume of the pumping chamber with the plunger, and wherein forcing the mixture in the pumping chamber to dispense the mixture can comprise reducing the volume of the pumping chamber with the plunger.

In another embodiment, the expansion of the pumping chamber with the plunger can cause simultaneous transport of reagent fluid and particles into the pumping chamber during at least a portion of the expansion of the pumping chamber. This may have the benefit of mixing the reagent fluid and the particles at the same time as they are loaded into the pumping chamber. In some examples, only one of the reagent fluid and the particles may be drawn into pumping chamber during a particular part of the expansion of the pumping chamber. However, during the at least a portion of the expansion of the pumping chamber both the particles and the reagent fluid can be drawn into the pumping chamber.

In another embodiment, the plunger can have a stroke. The motion of the plunger along at least a portion of the stroke can cause the simultaneous transport of reagent fluid and particles into the pumping chamber. The stroke of the plunger can be equivalent to the full range of motion of the plunger. During at least a portion of the full range of motion of the plunger (as the volume of the pumping chamber is being expanded), the reagent fluid and the particles can be drawn or loaded into the pumping chamber simultaneously. This may have the advantage of mixing the reagent fluid and the particles at the same time, as they are loaded into the pumping chamber. The simultaneous drawing of the particles and the reagent fluid may not be during the entire stroke of the plunger, it may only need to be a portion of the stroke.

In another embodiment, a single expansion of the pumping chamber can cause transport of both reagent fluid and particles into the pumping chamber. In some examples, the particles and the reagent fluid can be both drawn into the pumping chamber simultaneously. In other examples, the particles and the reagent fluid can be drawn into the pumping chamber sequentially.

In another embodiment, during a first part of the single expansion of the pumping chamber, only one of the reagent fluid and the particles can be transported into the pumping chamber. During a second part of the single expansion of the pumping chamber, both of the reagent fluid and the particles can be transported into the pumping chamber. In this example, the reagent fluid and particles do not always enter the pumping chamber at the same time (i.e., simultaneously) but subsequently within the same plunger stroke.

Embodiments may have the advantage during the withdrawal movement of the plunger defined volumes from both reservoirs can be sucked into the pumping chamber within the same plunger movement step and without any additional valve functionality needed, either simultaneously or subsequently as mentioned above.

In some prior art, a valve is used to alternatively connect different chambers to the pumping chamber. Embodiments may have the advantage that these additional valves may not be necessary. A further advantage that embodiments may have is that because the reagent fluid and the particles enter the pumping chamber during at least a portion of the stroke the reagent fluid and particles can be mixed during motion of the piston. This may reduce the need for an additional mixing step.

A cartridge for an automatic analyzer is presented. The cartridge can comprise a first reservoir at least partially filled with a reagent fluid. The cartridge can further comprise a second reservoir at least partially filled with particles. The cartridge can further comprise a pumping chamber formed from a cavity. The cartridge can further comprise at least one first pumping chamber conduit connecting the first reservoir and the pumping chamber. The cartridge can further comprise at least one second pumping chamber conduit connecting the second reservoir and the pumping chamber. The cartridge can further comprise an outlet for dispensing the reagent fluid and the particles from the cartridge. The cartridge can further comprise an outlet conduit connecting the outlet to the pumping chamber. The cartridge can further comprise a valve for sealing the outlet conduit.

In another embodiment, the pumping chamber can be formed from a cavity. The cartridge can further comprise a plunger movably mounted within the pumping chamber. The plunger can be configured for changing the volume of the pumping chamber.

In another embodiment, the particles can be dry within the second reservoir. That is to say that the particles are not mixed with a fluid within the second reservoir.

In another embodiment, the particles can be mixed with a buffer solution within the second reservoir. In some examples, the buffer solution can be the same as the reagent fluid. In other examples, the buffer solution may be different than the reagent fluid.

In another embodiment, the buffer solution can be a gel such as, for example, a thixotropic gel. The use of a gel may be beneficial because it may reduce sedimentation of the particles within the second reservoir.

In another embodiment, the buffer solution and the particles can form a colloidal suspension. In this example, the particles can be colloidally suspended within the buffer solution. This may provide for better and precise dispensing of particles into the pumping chamber.

In another embodiment, the particles can have a first specific gravity. The buffer solution can have a second specific gravity. The first specific gravity can be greater than the second specific gravity. In this embodiment, the particles in the buffer solution can naturally sediment within the second reservoir. In some examples, this may lead to a more uniform dispensing of particles from the second reservoir.

In another embodiment, the buffer solution comprised in the second reservoir can be identical to the reagent fluid comprised in the first reservoir. In another embodiment, this can be achieved by a porous divider located between the first reservoir and the second reservoir to allow the transfer of fluid between the first reservoir and the second reservoir but to retain the particles in the second reservoir.

In another embodiment, the reservoir can comprise a funnel structure and the funnel structure at least can partially form the pumping chamber conduit. This for instance may be useful for concentrating the particles such that they can be reproducibly dispensed into the pumping chamber.

In another embodiment, the cartridge may be placed into an operating position. In the operating position, the funnel structure can be above the pumping chamber.

In another embodiment, the particles can have a first specific gravity. The buffer solution can have a second specific gravity. The first specific gravity and the second specific gravity can differ by less than 5%. In other examples, the first specific gravity and second specific gravity can differ by less than 1%.

In another embodiment, the valve can be configured for sealing the at least one first pumping chamber conduit and the at least one second pumping chamber conduit when the pumping chamber is connected to the outlet conduit. The valve can be configured for sealing the outlet conduit when the at least one first pumping chamber conduit connects the first reservoir to the pumping chamber. The valve can be configured for sealing the outlet conduit when the at least one second pumping chamber conduit connects the second reservoir to the pumping chamber.

In another embodiment, the valve can be a rotary valve. The cavity can be within the rotary valve. The rotary valve can be rotated into at least a first position and a second position. In the first position, the outlet conduit can be aligned to connect the outlet to the pumping chamber. In the first position, the first pumping chamber conduit can be sealed from the pumping chamber.

In the first position, the pumping chamber can be sealed from the second pumping chamber conduit. In the second position, the outlet conduit can be sealed from the outlet. In the second position, the first pumping chamber conduit can be aligned to connect the first reservoir with the pumping chamber. In the second position, the at least one second pumping chamber conduit can be aligned to connect the second reservoir with the pumping chamber.

In some examples, the openings to the at least one first pumping chamber conduit and the at least one second pumping chamber conduit can be elongated. As the rotary valve turns the effective size of the openings to the at least one first pumping chamber conduit and the at least one second pumping chamber conduit can be adjusted. This may be useful in making a valve which can control the effective cross-section of the respective pumping chamber conduit and thereby the ratio of the reagent fluid to the particles that are transported into the pumping chamber.

In another embodiment, the valve can be a throttle valve configured to change the effective cross-section of the first pumping chamber conduit and/or the second pumping chamber conduit. This, for example, may be useful in controlling the ratio of reagent fluid to particles that are transported into the pumping chamber.

In another embodiment, the cartridge can comprise a first pumping chamber valve connected to the first pumping chamber conduit configured to change the effective cross-section of the first pumping chamber conduit and/or a second pumping chamber valve connected to the second pumping chamber conduit configured to change the effective cross-section of the second pumping chamber conduit. This may be useful for controlling the first defined volume relative to the second defined volume and thereby the mixing ratio of particles to reagent fluid In another embodiment, the cartridge can comprise multiple first pumping chamber conduits. In another embodiment, the valve can be configured for selecting at least one of the multiple first pumping chamber conduits to connect the first reservoir with the pumping chamber.

In the case of a rotary valve being used, different positions of the valve can be rotated into place to adjust which of the multiple first pumping chamber conduits is used. This may be useful for adjusting the relative fluid conductance from the two reservoirs.

In another embodiment, the cartridge can further comprise a first shutoff valve assembly for selectively opening or closing each of the first pumping chamber conduits.

In another embodiment, the cartridge can comprise multiple second pumping chamber conduits.

In another embodiment, the valve can be configured for selecting at least one of the multiple second pumping chamber conduits to connect to the second reservoir with the pumping chamber. In the case of a rotary valve, this embodiment can be effected by moving the valve into different rotational positions.

In another embodiment, the cartridge can further comprise a second shutoff valve assembly for selectively opening or closing each of the second pumping chamber conduits.

In another embodiment, the first pumping chamber conduit and the second pumping chamber conduit can join for form a common conduit. The common conduit can connect the pumping chamber to the first pumping chamber conduit and the second pumping chamber conduit.

In another embodiment, the pumping chamber can be configured for dispensing the maximum volume of about 1 ml.

In another embodiment, the particles can comprise any one of the following: magnetic beads, magnetized polystyrene beads, latex beads, glass beads, and combinations thereof.

In another embodiment, the particles can be coated for binding a biotinylated antibody or can be antibody coated.

In another embodiment, the coating for binding a biotinylated antibody can be streptavidin.

An advantage of using a cartridge for dispensing coated particles can be that these coated particles can be able to go through the narrow valve or pumping chamber conduit within a very short period of time in the millisecond range and still work properly in an analytical assay. That is to say transport of the coated particles through the second pumping chamber conduit may not damage their coatings such as streptavidin.

An automatic analyzer for performing a measurement on a sample containing an analyte is presented. The automatic analyzer can be operable for holding a cartridge according to an embodiment. The automatic analyzer can comprise an actuator assembly operable for applying a force to transport a first defined volume of reagent fluid and a second defined volume of particles into the pumping chamber. For example, if the cartridge comprises a plunger for the pumping chamber, the actuator may actuate the plunger. The actuator assembly may also be configured for actuating the valve.

In other examples, the actuator assembly may apply a negative or positive pressure to portions of the cartridge to force the reagent fluid and/or particles into the pumping chamber. The automatic analyzer can further comprise a controller for controlling the automatic analyzer. The controller for instance may be a processor or other controller which can be used to control or automate the automatic analyzer. The automatic analyzer can further comprise an analytical unit for performing a measurement.

In another embodiment, the automatic analyzer can further comprise a memory for storing machine-executable instructions. Execution of the instructions can cause the processor to close the valve by controlling the actuator assembly. Execution of the machine-executable instructions can further cause the processor to control the actuator assembly to apply a force to transport a first defined volume of reagent fluid and a second defined volume of particles into the pumping chamber to form a mixture of reagent fluid and particles. In one example, this may comprise expanding the volume of the pumping chamber with a plunger to draw a defined volume both of reagent fluid and particles into the chamber to form a mixture of reagent fluid and particles by controlling the actuator assembly. In other examples, this may comprise applying a positive or negative pressure to the pumping chamber and/or the first reservoir and/or the second reservoir. Execution of the machine-executable instructions can further cause the processor to open the valve by controlling the actuator assembly.

Execution of the machine-executable instructions can further cause the processor to control the actuator to force the mixture into the pumping chamber to dispense the mixture from the outlet into a fluid receptacle for mixing with the sample containing an analyte. For example, if the pumping chamber comprises a plunger, this may include reducing the volume of the pumping chamber with the plunger to dispense the mixture from the outlet into a fluid receptacle by controlling the actuator assembly. Execution of the machine-executable instructions can further cause the processor to perform a measurement on the sample by controlling the analytical unit.

In another embodiment, the analytical unit can be any one of the following: an electrochemiluminescence or ECL measurement system, an NMR system, an optical transmission measurement system, an optical reflectance measurement system, an electrochemical measurement system, an optical sensor, a pH meter, a camera system, a chromatography system, a mass spectrometer and combinations thereof.

A method of dispensing a mixture of particles and reagent fluid is presented. The cartridge can comprise a first reservoir at least partially filled with a reagent fluid. The cartridge can further comprise a second reservoir at least partially filled with particles. The cartridge can further comprise a pumping chamber. The cartridge can further comprise at least one first pumping chamber conduit connecting the first reservoir and the pumping chamber. The cartridge can further comprise at least one second pumping chamber conduit connecting the second reservoir and the pumping chamber. The cartridge can further comprise an outlet for dispensing the reagent fluid and the particles from the cartridge. The cartridge can further comprise an outlet conduit connection the outlet to the pumping chamber. The cartridge can further comprise a valve for sealing the outlet conduit.

The method can comprise closing the valve. The method can further comprise applying a force to transport a first defined volume of reagent fluid and second defined volume of particles into the pumping chamber to form a mixture of reagent fluid and particles. The pumping chamber can be pumped by a plunger. This may include expanding the volume of the pumping chamber with the plunger to draw defined volumes both of reagent fluid and particles. The method can further comprise opening the valve. The method can further comprise forcing the mixture from the pumping chamber to dispense the mixture from the outlet. For example, if the pumping chamber is actuated by a plunger, this may comprise reducing the volume of the pumping chamber with a plunger to dispense the mixture from the outlet.

In another embodiment, the particles can be magnetic beads. These for instance may be magnetized polystyrene beads. The particles may have a diameter between about 1 and about 4 µm. In another example, they may have a diameter between about 2 and about 3 µm and/or the particles can be latex beads.

In another embodiment, the particles can have a diameter between about 0.05 µm and about 0.4 µm.

In another embodiment, the beads can be streptavidin-coated for binding a biotinylated antibody.

In another embodiment, the particles may be magnetic. Segmentation of the particles may therefore be able to be controlled by turning on and off a magnet.

In another embodiment, the buffer solution can be water.

In another embodiment, the buffer solution can be a solution containing one or more of the following: salts, proteins, sugar, detergents, volatile components, lipids, antibodies, and other particles, and combinations thereof.

It can be understood that one or more of the aforementioned embodiments may be combined as long as the combined embodiments are not mutually exclusive.

Referring initially to FIG. 1, FIG. 1 shows an example of an automatic analyzer 100. The automatic analyzer can comprise a cartridge 102. The cartridge can be connected to an actuator 104. Below the cartridge 102 can be seen a sample holder 106 containing a sample containing the analyte 108. Adjacent to the sample holder 106 can be an analytical unit 110. The automatic analyzer 100 can also comprise a computer 112 which can be configured for controlling and operating the automatic analyzer 100.

The cartridge 102 can comprise a first reservoir 114 filled with a reagent fluid 116. The cartridge 102 can further comprise a second reservoir 118 filled with particles 119. The first reservoir 114 can be connected to a pumping chamber 126 by a first pumping chamber conduit 120. The second reservoir 118 can be connected to the pumping chamber 126 by a second pumping chamber conduit 122. The cartridge 102 can further comprise an outlet 124 which can be for dispensing a mixture of reagent fluid 116 and particles 119. In this example, the volume of the pumping chamber 126 can be adjusted by a plunger 128 which can be actuated by the actuator 104. The pumping chamber can be formed by a cavity 127. Movement of the plunger 128 within the cavity 127 can adjust the volume of the pumping chamber 126. Other embodiments are also envisioned such as applying a negative or positive pressure to the pumping chamber 126 and/or the first reservoir 114 and/or the second reservoir 118. The pumping chamber 126 can be connected to the outlet 124 by an outlet conduit 130. The outlet conduit 130 can be able to be opened or sealed by a valve 132. The outlet 124 can be positioned over the sample holder 106 so that the mixture of reagent fluid 116 and particles 119 can be dispensed into the sample holder to mix with the sample 108 containing the analyte. Once the mixture has been dispensed and mixed with the sample 108, a measurement can be performed by the analytical unit 110.

The valve 132, the actuator 104 and the analytical unit 110 are shown as being connected to a hardware interface 134 of the computer 112. The hardware interface can be connected to a processor 136. The hardware interface 134 can enable the processor 136 to control the other components of the automatic analyzer 100. The processor is further shown as being connected to computer storage 138 and computer memory 140. The processor 136 is shown as being further connected to an optional user interface 142. The computer storage 138 is shown as containing measurement data 150 that was measured by the analytical unit 110 on the sample 108 after the mixture of reagent fluid 116 and particles 119 have been added to it. The computer memory 140 is shown as containing a control module 152 which can enable the processor 136 to control the operation and function of the automatic analyzer 100 to acquire the measurement data 150. The computer storage 138 and computer memory 140 may be combined into a single storage unit. Also the contents of the computer storage 138 and computer memory 140 may be exchanged or duplicated between each other.

Figure 2:
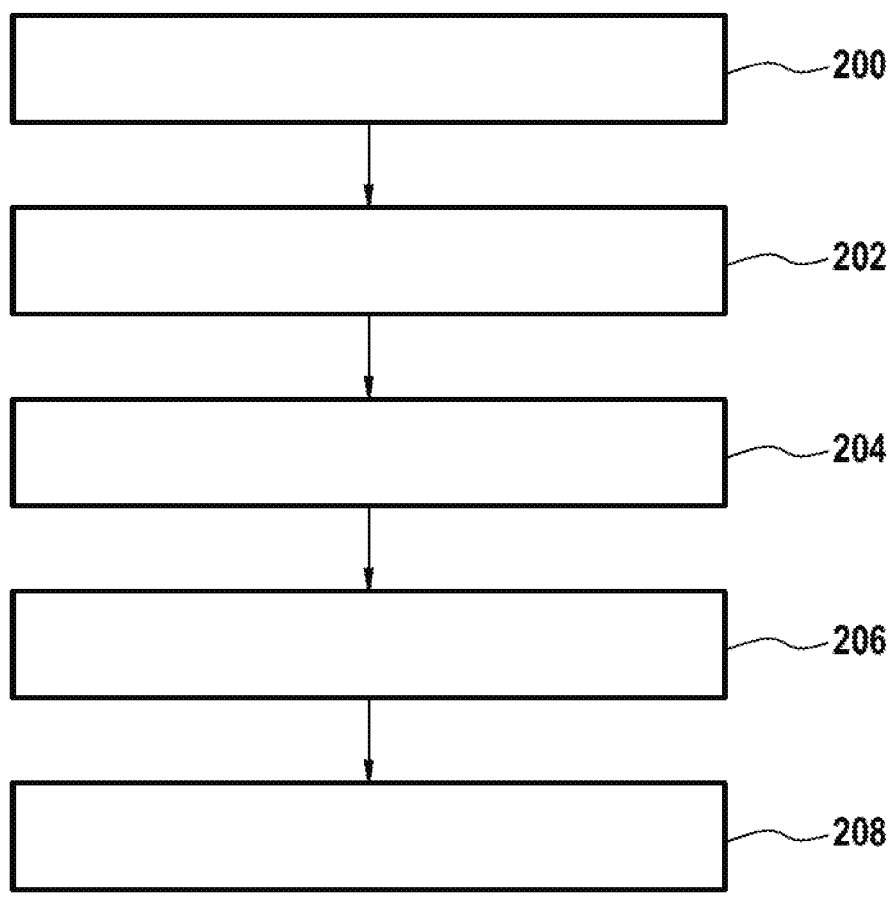
FIG. 2 illustrates a flow chart which shows a method of operating the automatic analyzer of FIG. 1 according to an embodiment of the present disclosure.

FIG. 2 shows a flowchart which illustrates a method of operating the automatic analyzer 100 of FIG. 1. First in step 200, the valve 132 can be closed. Next in step 202, a force can be applied to transport a first defined volume of reagent fluid 116 and a second defined volume of particles 119 into the pumping chamber 126 to form a mixture of reagent fluid and particles. In the specific example shown in FIG. 1, the plunger 128 can be withdrawn towards the actuator 104 to expand the volume of the pumping chamber 126. Next in step 204, the valve 132 can be open. Next in step 206, the mixture in the pumping chamber 126 can be forced to dispense the mixture from the outlet 124 into the fluid receptacle or sample holder 106. This can then cause the mixture to mix with the sample 108. Next in step 208, the processor 136 can control the analytical unit 110 to acquire the measurement data 150. The method of FIG. 2 may be modified. For example, the cartridge 102 can be operated without the computer system 112. The plunger 128 for example can be operated manually as well as the valve 132. The method of FIG. 2 can also be modified that the method can simply be to dispense the mixture of reagent fluid 116 and particles 119. It is not necessary that the mixture be dispensed into a sample holder or fluid receptacle 106.

Figure 3:
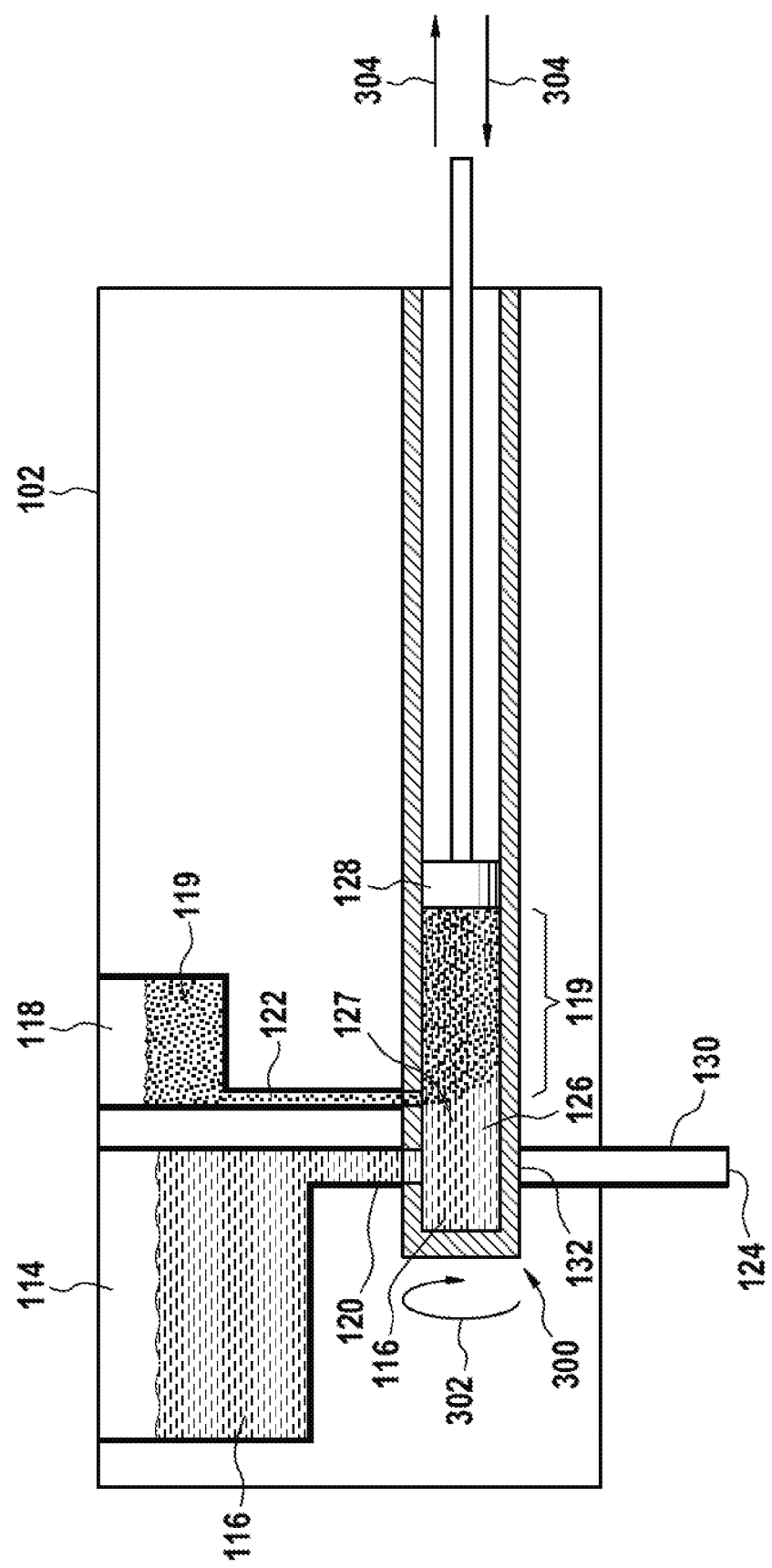
FIG. 3 illustrates an example of a cartridge according to an embodiment of the present disclosure.

FIG. 3 shows a further example of the cartridge 102. In this example, the valve 132 can be formed by a rotatable portion 300. The rotatable portion can be a cylindrical tube that also can form the pumping chamber 126. As the rotatable portion 300 is rotated the outlet conduit 130, the first pumping chamber conduit 120 and the second pumping chamber conduit 122 can be selectively connected or disconnected to the pumping chamber 126. In the view shown in FIG. 3, the first pumping chamber conduit 120 and the second pumping chamber conduit 122 are shown as being connected to the pumping chamber 126. If the rotatable portion 300 is rotated, then the first pumping chamber conduit and the second pumping chamber conduit 122 can be disconnected from the pumping chamber 126 and the outlet conduit 130 can be connected to the pumping chamber 126.

The arrows labeled 304 indicate the direction of travel of the piston 128. The movement of the piston 128 in these directions can indicate the stroke of the piston. The stroke of the piston can be the full range of motion that the piston is able to go through. The arrows 304 do not show the full range of motion, but do indicate the directions in which the piston 128 can travel.

An example for the calculation of the volume of bead-containing fluid to be retrieved out of the second reservoir to provide a defined number of beads in the pumping chamber is given as follows:

Calculation of the bead volume:

Volume of a bead $V_b = 4\pi/3 * r^3$

Hexagonal close packing (HCP) volume of beads $V_h = V_b/0.740$

Desired number of beads: N

Volume to be retrieved out of second reservoir: $V = V_h * N$

Example using the densest packing of particles possible (=HCP):

Beads with diameter=2.8 μm: radius r=1.4 μm

Volume of a bead $V_b = 4\pi/3 * r^3 = 11.5$ μm$^3$

Volume of HCP packed beads $V_h = V_b/0.740 = 15.5$ μm$^3$

Desired number of beads N=100 000-300 000

Volume to be retrieved out of second reservoir: $V = V_h * N = 1\ 550\ 000$ μm$^3$ - $4\ 650\ 000$ μm$^3$ = 1.55-4.65 nl Functionality of coated beads after dispensing step:

The functionality of coated beads is assured when the functional groups, for example the Streptavidin group, coated on the surface of the beads remains undamaged. If this functional coating is removed or damaged, for example by rubbing or abrasive forces by dispensing or sedimenting of the beads, the functionality of the beads can, of course, be impaired. The damage of coatings with the Streptavidin group can be detected. Therefore, a series of experiments were performed to check for the altering of Streptavidin surfaces of magnetic particles when being dispensed.

Experiment:

Measurement principle: The functionality of a bead can be affected if the functional Streptavidin group originally coated onto the surface of the bead is removed from the surface of the bead. Thus, an indicator for the impairment of the bead functionality can be the free Streptavidin in the supernatant.

The occurrence of free Streptavidin groups in the supernatant was tested using a Elecsys® 2010 system (Roche Diagnostics GmbH, Mannheim, Germany). For this experiment, a sample of magnetic beads coated with Streptavidin groups was divided into 3 aliquots. These aliquot groups were: a) a control group that was not dispensed, b) a group that was dispensed one time, and c) a group that was dispensed five times. The dispensing system used for this experiment was a Vermes dosing system (MDS 300 series, MDV 3010-70; Vermes Microdispensing GmbH, Otterfing, Germany), operated with 1.5 bar and using a dispensing tube with an inner diameter of 160 μm. The shear rate was approximately 600000 l/s.

At the beginning of the experiment, a homogeneous bead solution was separated into 15 tubes: 5 tubes were used as reference, 5 tubes were dosed 5 times and 5 tubes were dosed once with the Vermes dosing system (all at room conditions of 24° C. and 38% relative humidity). Eppendorf cups were used as collection vessels. The cups were arranged nearly horizontal during the dosing steps to avoid bubbles and extra shear stress. The fluid impinges on the vessel wall and not on the already contained fluid.

After the dosing steps, the magnetic particles were separated from the buffer using a magnetic separator. All Eppendorf cups have been put in the separator for one hour. The magnetic beads have been moved to the wall of the Eppendorf cups and the buffer solutions have been carefully removed with a pipette. These 15 buffer samples have been analyzed to determine the free Streptavidin (SA) within these "supernatant" samples. An antibody fragment comprising Biotin and Ruthenyl residues was used to detect the SA. A standard curve of different SA concentrations in buffer was prepared. A standard curve with 2 controls was measured to determine the function between signal and SA content. The SA content of all samples was determined. The difference between the SA content in the reference and the samples is an indicator for an impaired SA bead functionality.

Results of the experiment:
The results are summarized below

|  |  |
| --- | --- |
| Mean Ref | 230 |
| Mean 1xdosing | 228 |
| Mean 5xdosing | 248 |

No significant difference of the SA concentration can be found between the reference sample and sample dosed once. After five dispensing steps, a not significant increase of the free SA concentration in the buffer is detectable. This can lead to the conclusion that a short dispensing step with high shear rates does not destroy the chemical bonds between the bead surface and the functional group, SA.

The results show that there was no significant difference between the remaining functionality of the Streptavidin coating for the three groups. The Streptavidin coating on the magnetic particles was therefore not effectively damaged by the dispensing process or even after multiple dispensing processes.

Figure 4:
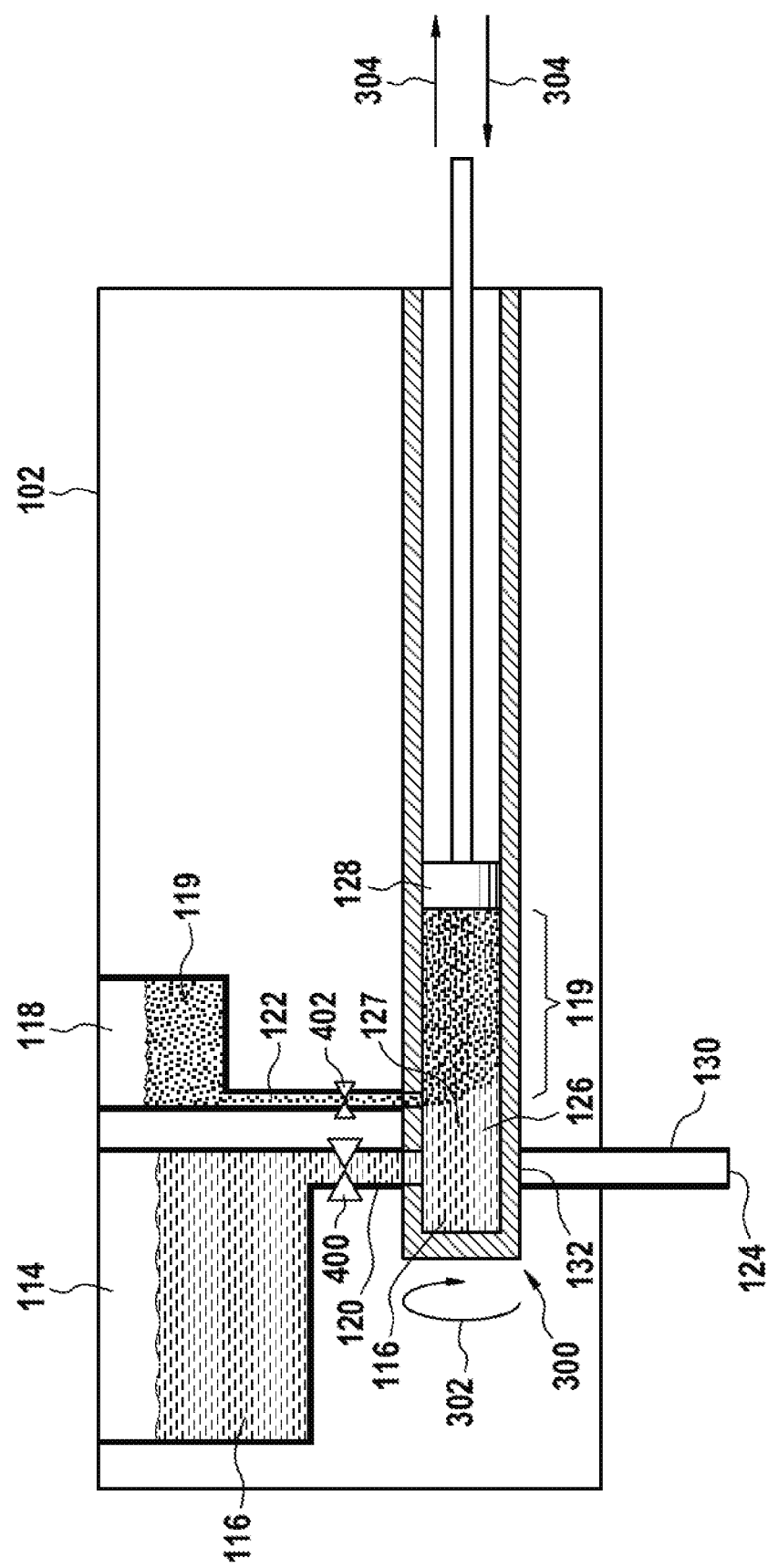
FIG. 4 illustrates a further example of a cartridge according to an embodiment of the present disclosure.

FIG. 4 shows a further modification of the cartridge 102. The cartridge of FIG. 4 is similar to that of FIG. 3 except there can be two additional valves shown. There can be a first shutoff valve assembly 400 which can be used as a valve on the first pumping chamber conduit 120 and there can be a second shutoff valve assembly 402 that can be used as a valve on the second pumping chamber conduit 122. These two valves 400, 402 may be used to shut off the two pumping chamber conduits 120, 122 and/or may be used to throttle or regulate the effective cross-section of the first pumping chamber conduit 120 or the second pumping chamber conduit 122 and thereby the flow from the first reservoir 114 or the second reservoir 118.

Figure 5:
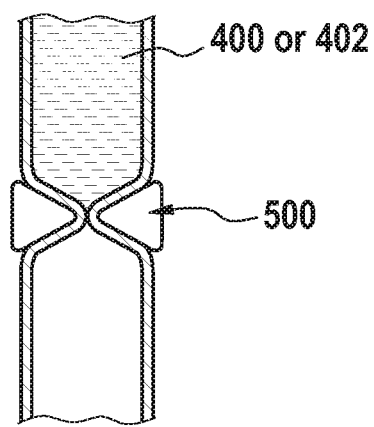
FIG. 5 illustrates an example of a pinch valve according to an embodiment of the present disclosure.

FIG. 5 shows an example of a pinch valve 500. The pinch valve 500 may be used to replace valve 400, 402 or 132.

Figure 6:
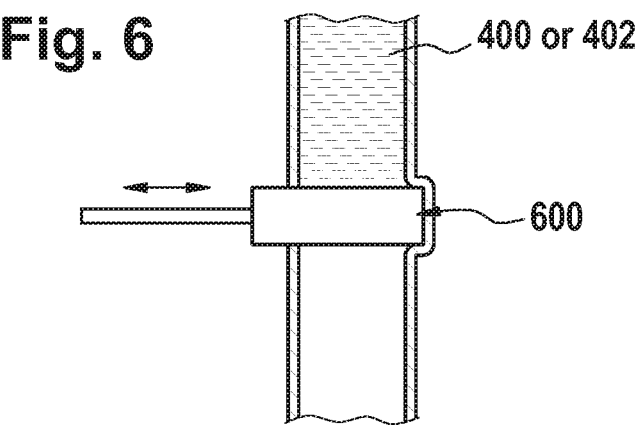
FIG. 6 illustrates an example of a slide valve according to an embodiment of the present disclosure.

FIG. 6 shows an example of a slide valve 600. The slide valve 600 may be used to replace the valve 400, 402 or 132.

Figure 7:
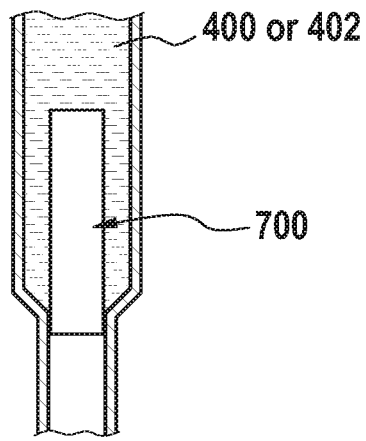
FIG. 7 illustrates an example of a piston valve according to an embodiment of the present disclosure.

FIG. 7 is an example of a piston valve 700. The piston valve 700 may be used to replace valve 400, 402 or valve 132. The valves 500, 600, 700 shown in FIGS. 5, 6 and 7 may be used to completely block the flow or may be used to throttle or constrict the amount of flow through a conduit.

Figure 8:
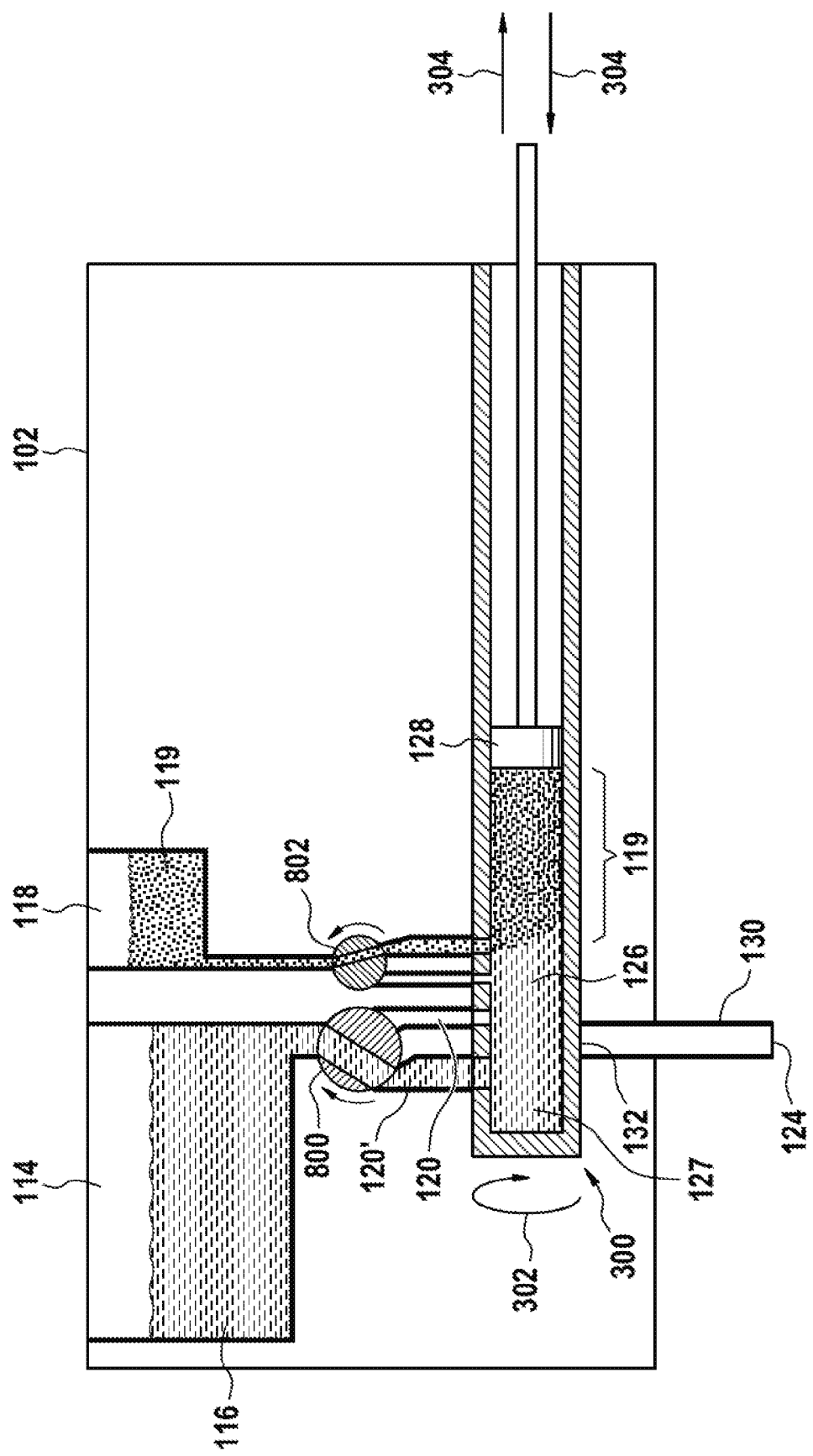
FIG. 8 illustrates a further example of a cartridge according to an embodiment of the present disclosure.

FIG. 8 shows a further modification of the cartridge 102 of FIG. 3. In this example, there can be more than one first pumping chamber conduit 120, 120'. There can be a first pumping chamber conduit 120 and an additional first pumping chamber conduit 120'. There can be then a first selector valve 800 to select between conduits 120 and 120'. Likewise, there can be more than one second pumping chamber conduit 122, 122'. There can be the second pumping chamber conduit 122 and an additional second pumping chamber conduit 122'. There can be a second selector valve 802 which can allow selection of conduit 122 or 122'. By actuating the valves 800 and 802, the flow rate of the reagent fluid 116 relative to the particles 119 can be controlled and the mixture of the reagent fluid to the particles 119 in the pumping chamber 126 can be controlled.

Figure 9:
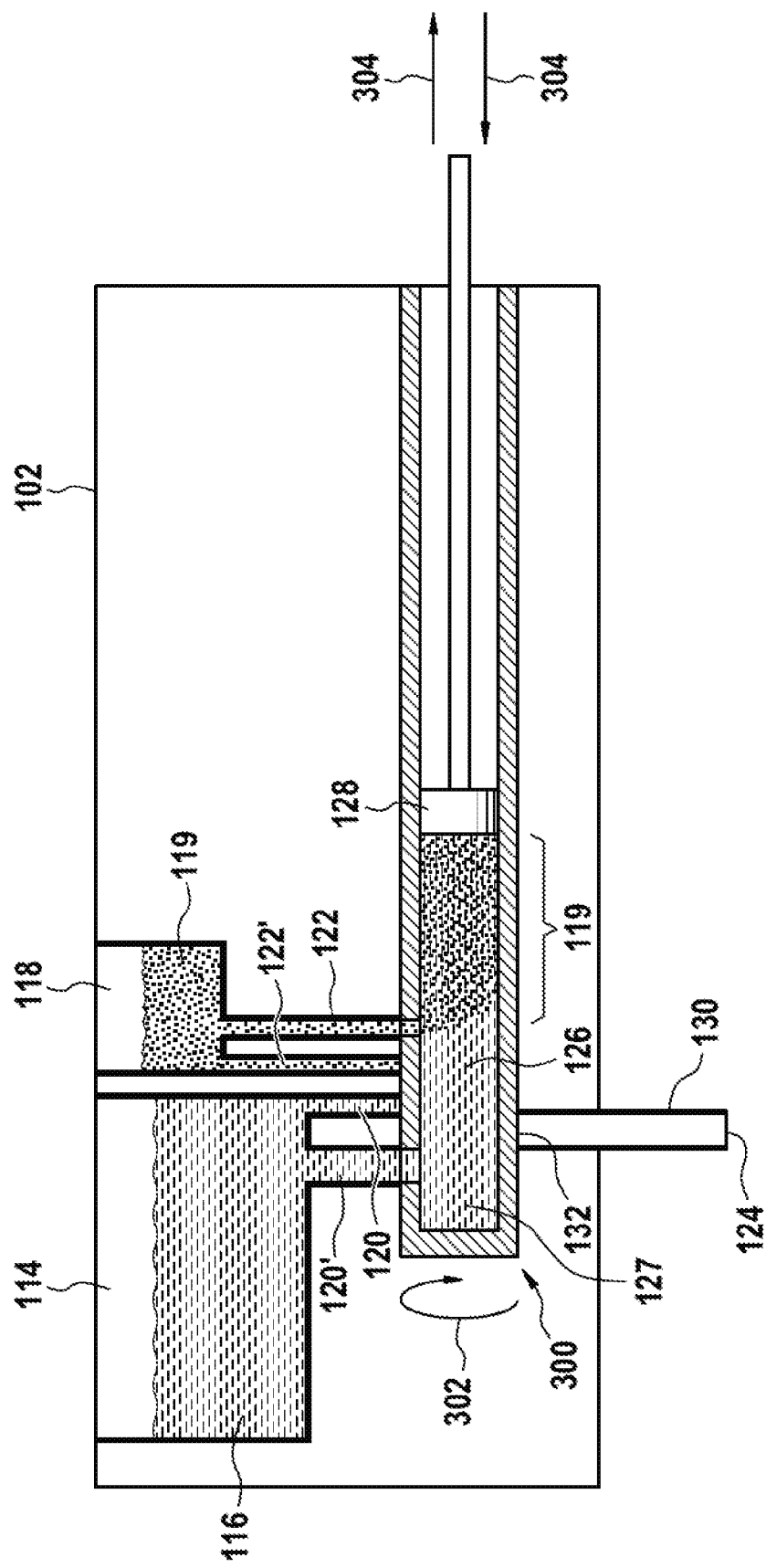
FIG. 9 illustrates a further example of a cartridge according to an embodiment of the present disclosure.

FIG. 9 shows a modification of the cartridge 102 of FIG. 8. Instead of having the first selector valve 800 and the second selector valve 802, the rotatable portion 300 can be rotated into various positions to select between the conduit 120 and 120' and also to select between conduit 122' and 122.

Figure 10:
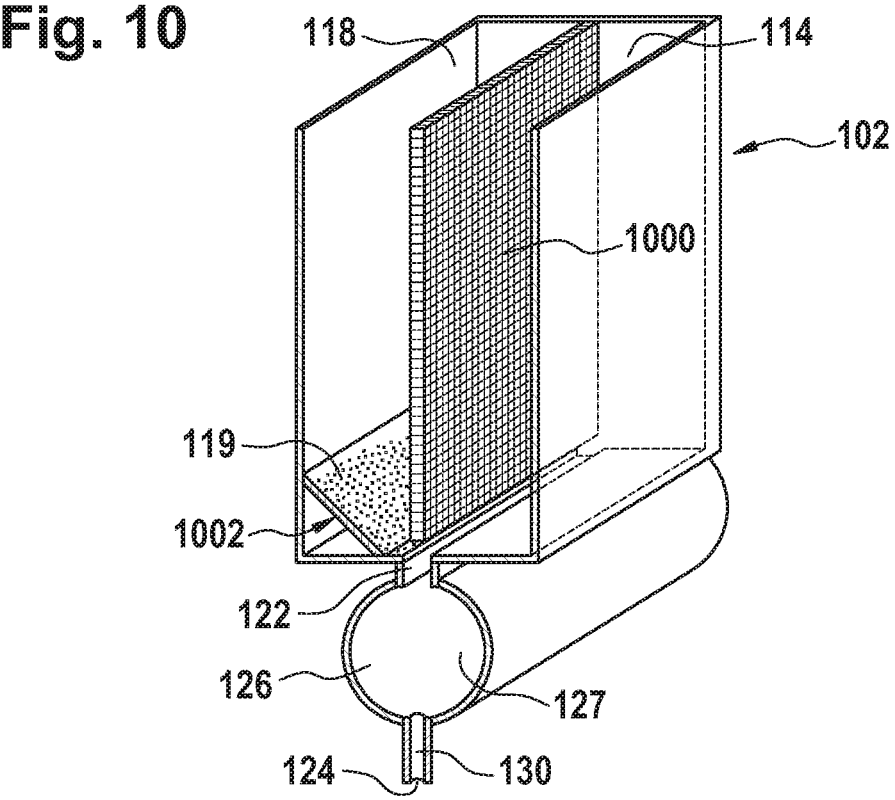
FIG. 10 illustrates a further example of a cartridge according to an embodiment of the present disclosure.

FIG. 10 shows a further modification of the cartridge 102. In this example, the first reservoir 114 and the second reservoir 118 can be separated by a porous structure 1000. The porous structure can allow the reagent fluid to flow back and forth between the first reservoir 114 and the second reservoir 118. The second reservoir 118 can further comprise a funnel-like structure 1002 that can accumulate the particles 119 in a dense and defined manner as they sediment. The funnel-like structure 1002 can also form part of the second pumping chamber conduit 122.

Figure 11:
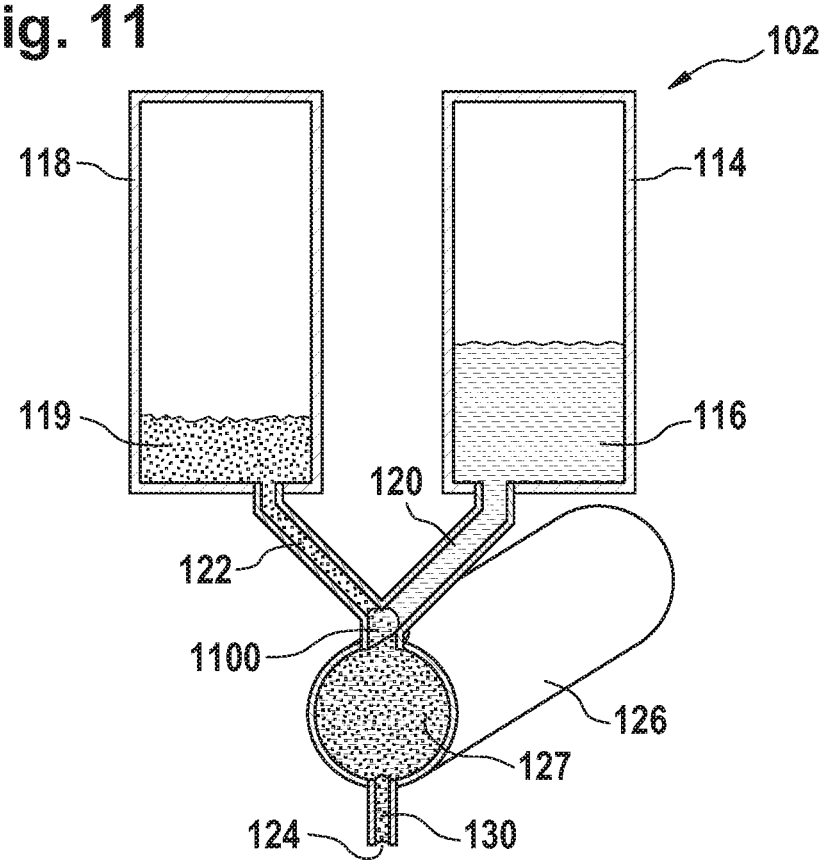
FIG. 11 illustrates a further example of a cartridge according to an embodiment of the present disclosure.

FIG. 11 shows a further modification of the cartridge 102. In this example, the first pumping chamber conduit 120 and the second pumping chamber conduit 122 can join to form a common conduit 1100. The common conduit 1100 can connect the first pumping chamber conduit 120 and the second pumping chamber conduit 122 both to the pumping chamber 126. The two conduits 120 and 122 can have different diameters and can be used to control the mix of particles 119 to fluid 116.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of performing a measurement on a sample containing an analyte using a cartridge, wherein the cartridge comprises a first reservoir at least partially filled with a reagent fluid, a second reservoir at least partially filled with particles, a pumping chamber, wherein the pumping chamber is formed from a cavity, wherein the cartridge further comprises a plunger mounted within the pumping chamber, wherein the plunger is configured for changing the volume of the pumping chamber, wherein the cartridge further comprises at least one first pumping chamber conduit connecting the first reservoir and the pumping chamber, at least one second pumping chamber conduit connecting the second reservoir and the pumping chamber, an outlet for dispensing the reagent fluid and the particles from the cartridge, an outlet conduit connecting the outlet to the pumping chamber, and a valve for sealing the outlet conduit, wherein a fluid conductivity of the outlet conduit is larger than a fluid conductivity of the at least one first pumping chamber conduit and a fluid conductivity of the at least one second pumping chamber conduit, the method comprising:
    closing the valve;
    applying a force to the plunger to transport a first defined volume of reagent fluid and a second defined volume of particles into the pumping chamber to form a mixture of reagent fluid and particles;
    opening the valve;
    forcing the mixture in the pumping chamber using the plunger to dispense the mixture from the outlet into a fluid receptacle for mixing with the sample containing an analyte; and performing the measurement on the sample containing an analyte using an analytical unit.

2. The method of claim 1, wherein applying a force to transport a first defined volume of reagent fluid and a second defined volume of particles into the pumping chamber to form a mixture of reagent fluid and particles comprises expanding the volume of the pumping chamber with the plunger, and wherein forcing the mixture in the pumping chamber to dispense the mixture comprises reducing the volume of the pumping chamber with the plunger.

3. The method of claim 2, wherein expansion of the pumping chamber with the plunger causes simultaneous transport of reagent fluid and particles into the pumping chamber during at least a portion of the expansion of the pumping chamber.

4. The method of claim 1, wherein the plunger has a stroke, wherein motion of the plunger along at least a portion of the stroke causes simultaneous transport of reagent fluid and particles into the pumping chamber.

5. The method of claim 1, wherein a single expansion of the pumping chamber causes transport of both reagent fluid and particles into the pumping chamber.

6. The method of claim 5, wherein during a first part of the single expansion of the pumping chamber only one of the reagent fluid and the particles is transported into the pumping chamber, wherein during a second part of the single expansion of the pumping chamber both of the reagent fluid and the particles are transported into the pumping chamber.

7. A cartridge for an automatic analyzer, the cartridge comprising:
    a first reservoir at least partially filled with a reagent fluid;
    a second reservoir at least partially filled with particles;
    a pumping chamber, wherein the pumping chamber is formed from a cavity;
    a plunger mounted within the pumping chamber, wherein the plunger is configured for changing the volume of the pumping chamber;
    at least one first pumping chamber conduit connecting the first reservoir and the pumping chamber;
    at least one second pumping chamber conduit connecting the second reservoir and the pumping chamber;
    an outlet for dispensing the reagent fluid and the particles from the cartridge;
    an outlet conduit connecting the outlet to the pumping chamber;
    and a valve for sealing the outlet conduit, wherein a fluid conductivity of the outlet conduit is larger than a fluid conductivity of the at least one first pumping chamber conduit and a fluid conductivity of the at least one second pumping chamber conduit.

8. The cartridge of claim 7, wherein the particles are mixed within a buffer solution within the second reservoir and wherein the particles have a first specific gravity, wherein the buffer solution has a second specific gravity, and wherein the first specific gravity is greater than the second specific gravity, wherein the buffer solution is the reagent fluid, wherein the first reservoir and the second reservoir are separated by a porous divider to allow the transfer of fluid between the first reservoir and the second reservoir.

9. The cartridge of claim 8, wherein the reservoir comprises a funnel structure, wherein the funnel structure at least partially forms the at least one second pumping chamber conduit.

10. The cartridge of claim 7, wherein the cartridge comprises a first pumping chamber valve connected to the first pumping chamber conduit configured to change the effective cross-section of the first pumping chamber conduit and a second pumping chamber valve connected to the second pumping chamber conduit configured to change the effective cross-section of the second pumping chamber conduit.

11. The cartridge of claim 7, wherein the cartridge comprises multiple first pumping chamber conduits and multiple second pumping chamber conduits, and wherein the cartridge comprises a selection means for selecting one of the multiple first pumping chamber conduits to connect the first reservoir with the pumping chamber and one of the multiple second pumping chamber conduits to connect the second reservoir with the pumping chamber.

12. The cartridge of claim 11, wherein the selecting means comprises a first selector valve configured for selecting one of the multiple first pumping chamber conduits to connect the first reservoir with the pumping chamber and a second selector valve is configured for selecting one of the multiple second pumping chamber conduits to connect the second reservoir with the pumping chamber.

13. The cartridge of claim 11, wherein the cartridge further comprises a first shutoff valve assembly for selectively opening or closing each of the first pumping chamber conduits and wherein the cartridge further comprises a second shutoff valve assembly for selectively opening or closing each of the second pumping chamber conduits.

14. An automatic analyzer for performing a measurement on a sample containing an analyte, wherein the automatic analyzer comprises the cartridge according to claim 7, the automatic analyzer further comprising:
an actuator assembly for actuating the plunger and the valve;
and an analytical unit for performing a measurement.

15. The automatic analyzer of claim 14, wherein the automatic analyzer further comprises,
a controller; and
a memory for storing machine executable instructions, wherein execution of the instructions cause the processor to:
close the valve by controlling the actuator assembly,
apply the force to the pumping chamber with the actuator to transport a fixed mixture of reagent fluid and particles into the pumping chamber to form a mixture of reagent fluid and particles by controlling the actuator assembly,
open the valve by controlling the actuator assembly,
force the mixture in the pumping chamber with the actuator to dispense the mixture from the outlet into a fluid receptacle by controlling the actuator assembly, and
perform the measurement on the sample containing an analyte by controlling the analytical unit.

16. A method of dispensing a mixture of particles and reagent fluid using a cartridge, wherein the cartridge comprises a first reservoir at least partially filled with a reagent fluid, a second reservoir at least partially filled with particles, a pumping chamber, wherein the pumping chamber is formed from a cavity, wherein the cartridge further comprises a plunger mounted within the pumping chamber, wherein the plunger is configured for changing the volume of the pumping chamber, wherein applying a force to transport a first defined volume of reagent fluid and a second defined volume of particles into the pumping chamber to form a mixture of reagent fluid and particles comprises expanding the volume of the pumping chamber with the plunger, and wherein forcing the mixture in the pumping chamber to dispense the mixture comprises reducing the volume of the pumping chamber with the plunger, at least one first pumping chamber conduit connecting the first reservoir and the pumping chamber, at least one second pumping chamber conduit connecting the second reservoir and the pumping chamber, an outlet for dispensing the reagent fluid and the particles from the cartridge, an outlet conduit connecting the outlet to the pumping chamber, and a valve for sealing the outlet conduit, wherein a fluid conductivity of the outlet conduit is larger than a fluid conductivity of the at least one first pumping chamber conduit and a fluid conductivity of the at least one second pumping chamber conduit, the method comprising:
closing the valve;
applying a force to the plunger to transport a first defined volume of reagent fluid and second defined volume of particles into the pumping chamber to form a mixture of reagent fluid and particles;
opening the valve; and
forcing the mixture from the pumping chamber using the plunger to dispense the mixture from the outlet.

17. The method of claim 16, wherein applying a force to transport a first defined volume of reagent fluid and a second defined volume of particles into the pumping chamber to form a mixture of reagent fluid and particles comprises expanding the volume of the pumping chamber with the plunger, and wherein forcing the mixture in the pumping chamber to dispense the mixture comprises reducing the volume of the pumping chamber with the plunger.

18. The method of claim 17, wherein expansion of the pumping chamber with the plunger causes simultaneous transport of reagent fluid and particles into the pumping chamber during at least a portion of the expansion of the pumping chamber.

19. The method of claim 16, wherein the plunger has a stroke, wherein motion of the plunger along at least a portion of the stroke causes simultaneous transport of reagent fluid and particles into the pumping chamber.

20. The method of claim 16, wherein a single expansion of the pumping chamber causes transport of both reagent fluid and particles into the pumping chamber.

21. The method of claim 20, wherein during a first portion of the single expansion of the pumping chamber only one of the reagent fluid and the particles is transported into the pumping chamber, wherein during a second portion of the single expansion of the pumping chamber both of the reagent fluid and the particles are transported into the pumping chamber.

* * * * *